(12) United States Patent
Bissery et al.

(10) Patent No.: US 7,851,443 B2
(45) Date of Patent: Dec. 14, 2010

(54) COMBINATION COMPRISING COMBRETASTATIN AND ANTICANCER AGENTS

(75) Inventors: Marie-Christine Bissery, Vitry sur Seine (FR); Patricia Vrignaud, Combs la Ville (FR); Marielle Chiron-Blondel, Paris (FR); Brigitte Demers, Paris (FR)

(73) Assignee: Aventis Pharma SA, Antony (FR)

( * ) Notice: Subject to any disclaimer, the term of this patent is extended or adjusted under 35 U.S.C. 154(b) by 0 days.

(21) Appl. No.: 12/142,130

(22) Filed: Jun. 19, 2008

(65) Prior Publication Data

US 2009/0023656 A1 Jan. 22, 2009

(30) Foreign Application Priority Data

Dec. 22, 2005 (FR) ................... 05 13114

(51) Int. Cl.
*A61K 38/00* (2006.01)

(52) U.S. Cl. ...................................... 514/12

(58) Field of Classification Search ....... None
See application file for complete search history.

(56) References Cited

U.S. PATENT DOCUMENTS

| 4,996,237 A | 2/1991 | Pettit et al. |
| 5,430,062 A | 7/1995 | Cushman et al. |
| 5,525,632 A | 6/1996 | Obsumi et al. |
| 5,561,122 A | 10/1996 | Pettit |
| 5,674,906 A | 10/1997 | Hatanaka et al. |
| 5,731,353 A | 3/1998 | Ohsumi et al. |
| 6,933,320 B2 | 8/2005 | Bissery |
| 2005/0032699 A1 | 2/2005 | Holash et al. |

FOREIGN PATENT DOCUMENTS

| WO | WO 00/75319 A1 | 12/2000 |
| WO | WO 03/035008 | 5/2003 |
| WO | WO2005/000895 | 1/2005 |
| WO | WO 2005000895 A2 * | 1/2005 |
| WO | WO 2005027972 A2 * | 3/2005 |

OTHER PUBLICATIONS

Holash et al. (PNAS 2002; 99: 11393-11398).*
Hori et al. (British Journal of Cancer; 2002; 86: 1604-1614).*
Wiesenthal (http://weisenthal.org/feedback.html, Feb. 4, 2002.*
Tallarida (Drug Synergism and Dose-effect Analysis, Chapman & Hall/CRC, Boca Raton, 2000, pp. 1-13).*
Berenbaum ("Synergy, additivism and antagonism in immunosuppression," Clin exp Immunol 28:1-18, 1977).*

* cited by examiner

*Primary Examiner*—Brandon J Fetterolf
(74) *Attorney, Agent, or Firm*—Jiang Lin

(57) ABSTRACT

This invention relates to therapeutic combinations comprising VEGF Trap and a stilbene derivative, and to methods for treatment of cancer comprising administration of such combinations.

7 Claims, No Drawings

SEQUENCE LISTING

<160> NUMBER OF SEQ ID NOS: 1

<210> SEQ ID NO 1
<211> LENGTH: 458
<212> TYPE: PRT
<213> ORGANISM: Artificial
<220> FEATURE:
<223> OTHER INFORMATION: VEGFR1R2-Fc(delta)C1(a)

<400> SEQUENCE: 1

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr

-continued

```
                85                  90                  95
Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
            115                 120                 125

Asp Val Val Leu Ser Pro Ser His Gly Ile Glu Leu Ser Val Gly Glu
130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
            195                 200                 205

Tyr Thr Cys Ala Ala Ser Ser Gly Leu Met Thr Lys Lys Asn Ser Thr
            210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
                260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
            290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
            435                 440                 445

Gln Lys Ser Leu Ser Leu Ser Pro Gly Lys
450                 455
```

COMBINATION COMPRISING COMBRETASTATIN AND ANTICANCER AGENTS

The present invention relates to therapeutic combinations comprising a stilbene derivative and an anticancer agent, such as a VEGF inhibitor.

VEGF inhibitors, which are inhibitors of vascular endothelial growth factor, are in the majority of cases biological products chosen from soluble receptors, antisenses, RNA aptamers and antibodies.

The invention relates to the treatment of cancers, more especially of solid tumors, with combinations of stilbene derivatives and a VEGF inhibitor, to the use of this combination for an improved treatment against cancers, and to uses of these effective components for the treatment (therapy), suppression and remission of tumors and the like.

Today, a wide variety of chemotherapeutic agents are used for the treatment and suppression of tumors, especially malignant solid tumors. Although these agents can have a reducing effect on the tumors, it is often impossible for these known agents to bring about a recovery because of the acquisition of resistance against the agent by the cancer, the recurrence of the tumors, and so on. Consequently, other, more effective antitumor agents are required.

Although it is known that stilbene derivatives that have a cis-stilbene as the main backbone have strong mitosis-inhibiting activities and cytotoxicity, most stilbene derivatives are not yet available as pharmaceutical agents because of their low water-solubility.

It has recently been discovered that certain stilbene derivatives that have an inhibitory activity on tubulin polymerization also have an improved water-solubility. Such derivatives comprise the phosphorylated precursor of combretastatin-A4 (see U.S. Pat. No. 5,561,122) and the stilbene derivatives described in U.S. Pat. No. 5,674,906. The clinical use of these stilbene derivatives is seen as promising.

An object of the present invention is to develop a combination of antitumor agents which has a high efficacy, specifically to develop a pharmaceutical preparation capable of improving the efficacy of a stilbene derivative and, in particular, to develop and provide antitumor agents which are safe to use and have a higher efficacy in the treatment of malignant tumors.

It has been found that a stilbene derivative, administered together with another anticancer agent such as a VEGF inhibitor, has improved therapeutic effects for inhibiting tumor development.

The description and the preparation of the VEGF inhibitor preferably used in the invention, which is a VEGF Trap chimeric protein, are described in patent application WO00/75319. There are several embodiments of the chimeric protein.

The embodiment corresponding to VEGF Trap is that described in figure 24 (sequence; SEQ ID No: 1) in the patent application WO 00/75319. The VEGF Trap used in the invention is a fusion protein comprising the VEGFR1 signal sequence fused to the Ig domain D2 of the VEGFR1 receptor, itself fused to the Ig domain D3 of the VEGFR2 receptor, in turn fused to the IgG1 Fc domain, also called VEGFR1 R2-FcΔC1 or Flt1D2.Flk1D3.FcΔC1.

It has now been found that this new anticancer agent in combination with a stilbene derivative is especially effective in the treatment of solid tumors. Among the effective stilbene derivatives are combretastatin A-4 and a derivative of the compound, (Z)-1-(3-amino-4-methoxyphenyl)-2-(3,4,5-trimethoxyphenyl)ethene, which will be referred to as product of formula II. These two compounds exhibit strong mitosis-inhibiting activities and cytotoxicity, and they inhibit tubulin polymerization.

Combretastatin A-4 has the following formula:

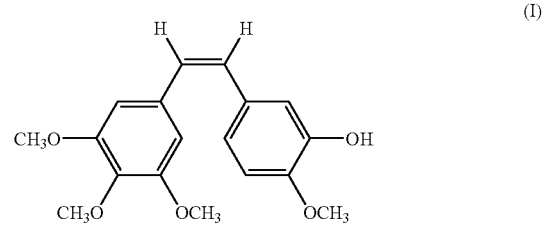

(I)

The product of formula (II) has the following formula:

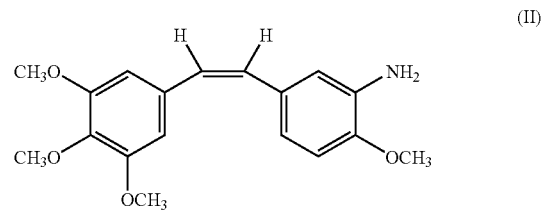

(II)

These combretastatins are barely water-soluble and they can be used in the form of a salt, for example hydrochloride, acetate, phosphate, methanesulfonate and the amino acid salt.

The production of the stilbene derivatives which can be in the form of pharmaceutically acceptable salts, of hydrates and of solvates, and the production of oral and/or parenteral pharmaceutical compositions containing the above compound, carrier(s) thereof and/or pharmaceutically acceptable diluent(s) thereof are described in U.S. Pat. Nos. 5,525,632, 5,731,353 and 5,674,906 for the product of formula (II) and the precursor. These patents, which are incorporated into this document by way of reference, reveal that, when they are used alone, the stilbene derivatives, including the combretastatin product of formula (II), have cancerostatic effects in vivo.

It has recently been discovered that the combination of the serine salt of combretastatin of formula (II) with VEGF Trap significantly reduces the development of the tumor volume compared with what is predicted, after the administration of each compound alone to mammals bearing tumors.

Consequently, the present invention is promising since it provides a new antitumor agent, for example a chemotherapeutic medicament against cancer (cancer chemotherapy agent), simultaneously or separately comprising two types of active ingredients, namely a stilbene derivative and VEGF Trap.

The present invention also encompasses a combination therapy in which the stilbene derivative and VEGF Trap are prepared as two separate pharmaceutical preparations and are administered to a patient in need thereof, simultaneously, semi-simultaneously, separately or sequentially.

The tumor against which the antitumor agents of the present invention are administered encompasses all types of tumors that appear in an animal, especially in a human being. Preferably, the antitumor agents of the present invention can be used to inhibit the proliferation of tumor cells in a human being. The antitumor agents of the present invention are pharmaceutical preparations in which at least two compounds are used to cure, treat, or suppress tumors.

There is no particular limitation to the administration form of the antitumor agents. Anticancer agents are routinely administered intravenously, parenterally and orally. The present invention also encompasses an antitumor agent comprising the combination of two compounds having distinct administration forms.

The stilbene derivative used in the present invention has a cis-stilbene as the main backbone and it exhibits an in vivo inhibitory activity on tubulin polymerization and/or an antitumor activity. The stilbene derivatives of the present invention also comprise precursors which can be converted in vivo into a stilbene derivative. All the appropriate, pharmaceutically acceptable derivative forms, such as salts, esters, amides, solvates (solvation products) and hydrates thereof, can be used as stilbene derivatives in the present invention, provided that the derivatives exhibit antitumor activity when they are used in vivo.

The precursors of the product of formula (II) are preferably amino acid salts.

The amino acids can be listed by α amino acids, β amino acids and γ amino acids. Examples of preferred amino acids include glycine, alanine, leucine, serine, lysine, glutamic acid, aspartic acid, threonine, valine, isoleucine, ornithine, glutamine, asparagine, tyrosine, phenylalanine, cysteine, methionine, arginine, β-alanine, tryptophan, proline, histidine, etc. In particular, threonine and serine are preferred in view of the pharmaceutical effects and safety for use. Although all these amino acids can be in the L, D or DL form, the L form is preferred.

As was described above, the stilbene derivative of the present invention is a compound that has a cis-stilbene backbone in its structure and it exhibits an inhibitory activity on tubulin polymerization and/or an antitumor activity. Such stilbene derivatives are illustrated by combretastatin A-4 and the product of formula (II) described in prior art publications, such as U.S. Pat. Nos. 4,996,237, 5,561,122 and 5,430,062. The stilbene derivatives of the prior art, described in these patent publications, and the combretastatin of formula (II) described in U.S. Pat. Nos. 5,525,632 and 5,731,353, can be used for the stilbene derivatives of the present invention, insofar as they correspond to the definition of the stilbene derivatives in the present invention.

The abovementioned stilbene derivatives can be produced by routine techniques comprising the methods described in the abovementioned known publications.

Among the stilbene derivatives of the present invention are salts, esters and other derivatives of stilbene, and derivatives which can be converted in vivo to stilbene derivatives, insofar as the stilbene derivatives manifest the abovementioned objective activities in an animal's body.

Among the compounds represented by general formula (II) above, are the compounds represented by formula (IIa) below:

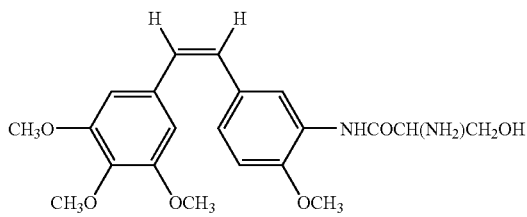

(IIa)

A compound of formula (IIa) is water-soluble and it may be in the form of a salt, for example hydrochloride, acetate, methanesulfonate and the like.

As a result, for the objectives of the present invention, the combinations are not exclusively limited to those which are obtained by a physical association of the constituents, but they also encompass those which allow a separate administration, which may be simultaneous or spaced out over a period of time.

One of the preferred embodiments in the present invention is the use of an effective amount of a compound IIa for inhibiting tumor growth in combination with VEGF Trap.

The antitumor agents of the present invention can be administered parenterally, as was discussed above. In this case, the antitumor agent can be administered intravenously as a bolus or prepared in an intravenous infusion bag, with pharmaceutically acceptable vectors, by various methods known to those skilled in the art. Preferably, the pharmaceutical agent is produced by a routine technique, for example in a unit pharmaceutical form and in the form of a lyophilized preparation, and it is again prepared in water or in another liquid infusion suitable for administration.

The ratio of the two components for the pharmaceutical preparation for the antitumor agent of the present invention can vary within a wide range, according to a certain number of factors such as the desired administration amount and the vector pharmaceutically acceptable for use. As regards the amounts or the combination in the administration of the stilbene derivative in the pharmaceutical preparation as antitumor agent of the present invention, the stilbene derivative is preferably used in an amount of approximately 0.01 to 100, and in particular approximately 0.1 to 10 parts by weight per 1 part by weight of VEGF Trap present in the pharmaceutical preparation. Thus, when the pharmaceutical preparation in the present invention containing two active ingredients must be administered to the patient, it is administered in an amount which would give the administration range defined above.

If the pharmaceutical preparation must be administered in stages, the administration range defined above may be established as the average ratio for the separate pharmaceutical preparations.

The present invention is now explained in greater detail with reference to preferred embodiments thereof. It should be noted that said embodiments are given only by way of example and they are not intended to limit the invention.

The efficacy of a combination can be demonstrated by determining its therapeutic synergy. A combination shows therapeutic synergy if it is therapeutically superior to the best agent used alone at its optimum dose (T. H. Corbett et al., Cancer Treatment Reports, 66, 1187 (1982)).

The efficacy of a combination can also be demonstrated by comparing the maximum tolerated dose of the combination with the maximum tolerated dose of each of the separate constituents in the study in question. This efficacy can be quantified, for example by the $\log_{10}$ cell kill, which is determined by the following formula:

$$\log_{10} \text{cell kill} = T\text{-}C\ (\text{days})/3.32 \times T_d$$

in which T-C represents the delay in tumor growth, which is the average time, in days, taken by the tumors of the treated group (T) to reach a predetermined value (1 g for example) and for the tumors of the control group (C) to reach the same value, and $T_d$ represents the time, in days, necessary for the volume of the tumors in the control group to double. During the exponential phase of tumor growth (T. H. Corbett et al., Cancer, 40, 2660.2680 (1977); F. M. Schabel et al., Cancer Drug Development, Part B, Methods in Cancer Research, 17, 3-51, New York, Academic Press Inc. (1979)). A product is considered to be active if the $\log_{10}$ cell kill is greater than or equal to 0.7. A product is considered to be highly active if the $\log_{10}$ cell kill is greater than 2.8.

The combination, used at its own maximum tolerated dose, in which each of the constituents is present at a dose that generally does not exceed its maximum tolerated dose, will show therapeutic synergy when the $\log_{10}$ cell kill is at least 1 $\log_{10}$ greater than the value of the $\log_{10}$ cell kill of the best constituent when the latter is administered alone.

The inhibition of tumor growth results from a response to a therapy comprising the administration of an effective amount of combretastatin and an effective amount of a second anticancer compound as described below to a human being suffering from cancer. In an acceptable case, this administration suppresses tumor growth and, as a result, decreases the measurable size of the tumors. In an optimal case, the tumor undergoes complete regression.

As was described above, there is no particular limitation to the method of administering the antitumor agents of the present invention to the mammal treated. They can be administered orally or parenterally, for instance intravenously, subcutaneously or intramuscularly. For rapid efficacy, parenteral administration of combretastatin, such as by intravenous administration, as a bolus or by infusion, is preferred. In the method for administering the pharmaceutical preparation according to the present invention, the combretastatin can be administered simultaneously with another anticancer agent or the two can be administered sequentially in an optional order. The optimal method and the optimal sequence for administering combretastatin and the second anticancer agent can be suitably chosen by those skilled in the art by means of routine technique and the information contained in the present report.

An effective amount, combining combretastatin with VEGF Trap and inhibiting tumor growth, corresponds to a curative unit that can be administered to the human being suffering from a tumor sensitive to the constituents of this combination. The practically desirable curative unit varies according to the individual pharmaceutical forms of the combretastatin used, the individual pharmaceutical forms of the secondary anticancer used, the individual tumor cells being treated and the individual hosts being treated. The optimal curative doses for given pre-established conditions can be suitably chosen by those skilled in the art by means of test curative units and the information contained in the present report.

The antitumor agent of the present invention is a pharmaceutical preparation comprising at least combretastatin and VEGF Trap as described above, in such a way that the two active ingredients can be contained in the form of a mixture in a pharmaceutical preparation. However, the two active ingredients in the present invention can also be contained separately in distinct pharmaceutical preparations to be used sequentially and in combination. It should be noted that such a pharmaceutical preparation containing other agents (third and fourth medical components and so on) such as other antitumor agents can be naturally included by the present invention, insofar as the effective components used in the present invention are contained in the pharmaceutical preparation. In addition, it is possible for the pharmaceutically acceptable vectors, diluents and other substances, for any one of the pharmaceutical preparations in the present invention (a single pharmaceutical preparation containing the two components in the present invention and separate pharmaceutical preparations, each separately containing one of the two components for use in combination), to be contained in the antitumor agent of the present invention.

The present invention is now explained in greater detail with reference to preferred embodiments thereof. It should be noted that said embodiments are given only by way of examples and they are not intended to limit the invention.

The pharmaceutical preparations for infusion were prepared in accordance with the following composition using the compounds, combretastatins of formula (IIa) and A4, represented, respectively, by the chemical formulae which follow:

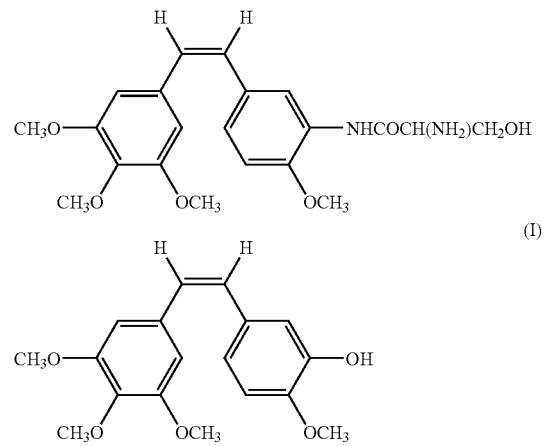

| | |
|---|---:|
| compound (I) (in phosphate form) and | 10 mg |
| physiological saline | 9.5 ml |
| compound (IIa) (in hydrochloride form) 0.5 ml and | 5 mg |
| physiological saline | 9.5 ml |

Antitumor Effect and Tests

The efficacy of the combinations of solid tumors can be determined experimentally in the following way:

The animals subjected to the experiment are female C3H/HeN mice which are bilaterally grafted subcutaneously with 30 to 60 mg of a fragment of MA13/C murine mammary adenocarcinoma tumor at day 0. In the case of an early tumor treatment, the implanted animals are distributed randomly in various groups which are or are not (controls) intended to receive the treatment(s). Where it is a question of treatment of advanced tumors, the animals bearing tumors having reached a pre-defined tumor size greater than 200 mg are distributed in the various treatment and control groups in such a way that the tumor size range is comparable from one group to the other. The animals which do not bear tumors can also be subjected to the same treatments as the animals bearing tumors, so that it is possible to dissociate the toxic effect from the specific effect on the tumor. Generally, the chemotherapy begins from 3 to 22 days after the graft, according to the type of tumor and the desired tumor size. The animals are observed and weighed every day. A dose which induces a weight loss of 20% or more at the lowest point (average of the group) or a mortality of 10% or more is considered to be toxic. The tumoral activity is evaluated at the highest nontoxic dose.

The tumors are measured 2 or 3 times a week until the tumor reaches approximately 2 g or until the animal dies, if this occurs before the tumor reaches 2 g. The animals are autopsied when they are sacrificed.

The antitumor activity is determined in accordance with various recorded parameters, such as the dose (mg/kg), the method of administration, the administration time, the toxicity and the log cell kill, which depends on the delay in tumor growth and also on the tumor doubling time.

| Agent (batch) | Route | Dosage per administration in mg/kg | Scheme (days) | Total dose in mg/kg | Mortality related to the agent (day of death) | Average weight loss as % per mouse at the lowest point (day of the lowest point) | Time to reach tumor size of 1000 mg (median) in days | T-C (days) | Log cell kill | Regression Partial | Complete | Comments |
|---|---|---|---|---|---|---|---|---|---|---|---|---|
| VEGF Trap | SC 0.1 ml | 40.0 | 21, 25 | 80.0 | 0/5 | 1.3 (23) | 24.6 | 0.8 | 0.1 | 0/5 | 0/5 | MAD inactive |
| | | 25.0 | | 50.0 | 0/5 | 1.8 (23) | 26.6 | 2.8 | 0.4 | 0/5 | 0/5 | Inactive |
| | | 10.0 | | 20.0 | 0/5 | 0.4 (23) | 24.2 | 0.4 | 0.1 | 0/5 | 0/5 | Inactive |
| Formula (IIa) | IV 0.4 ml | 93.5 | 21, 25 | 187.0 | 1/5 (23) | 7.4 (26) | — | — | — | — | — | Toxic |
| | | 58.0 | | 116.0 | 0/5 | 3.8 (22) | 28.9 | 5.1 | 0.6 | 0/5 | 0/5 | HNTD inactive |
| | | 36.0 | | 72.0 | 0/5 | 2.1 (22) | 27.9 | 4.1 | 0.5 | 0/5 | 0/5 | Inactive |
| | | 22.3 | | 44.6 | 0/5 | 0.6 (22) | 27.2 | 3.4 | 0.4 | 0/5 | 0/5 | Inactive |
| Formula (IIa) VEGF Trap | IV 0.4 ml SC 0.1 ml | 93.5 40.0 | 21, 25 21, 25 | 187.0 80.0 | 1/6 (27) | 16.3 (26) | — | — | — | — | — | Toxic |
| | | 58.0 40.0 | | 116.0 80.0 | 0/6 | 11.0 (26) | 34.2 | 10.4 | 1.3 | 2/6 | 0/6 | MTD active |
| | | 58.0 25.0 | | 116.0 50.0 | 0/6 | 13.2 (26) | 34.9 | 11.1 | 1.4 | 3/6 | 0/6 | Active |
| | | 58.0 10.0 | | 116.0 20.0 | 0/6 | 9.6 (26) | 33.4 | 9.6 | 1.2 | 0/6 | 0/6 | Active |
| | | 36.0 40.0 | | 72.0 80.0 | 0/6 | 7.4 (26) | 34.4 | 10.6 | 1.3 | 0/6 | 0/6 | Active |
| | | 35.0 25.0 | | 72.0 50.0 | 0/6 | 7.2 (27) | 33.3 | 9.5 | 1.2 | 0/6 | 0/6 | Active |
| | | 35.0 10.0 | | 72.0 20.0 | 0/6 | 8.9 (26) | 33.3 | 9.5 | 1.2 | 0/6 | 0/6 | Active |
| | | 22.3 40.0 | | 44.6 80.0 | 0/6 | 4.7 (27) | 33.3 | 9.5 | 1.2 | 0/6 | 0/6 | Active |
| | | 22.3 25.0 | | 44.6 50.0 | 0/6 | 5.9 (27) | 32.0 | 8.2 | 1.0 | 0/6 | 0/6 | Active |
| | | 22.3 10.0 | | 44.6 20.0 | 0/6 | 3.6 (26) | 30.2 | 6.4 | 0.8 | 0/6 | 0/6 | Active |
| Control | — | — | — | — | — | — | 23.8 | | | | | |

Tumor doubling time = 2.4 days.
Median tumor size per group at the beginning of treatmnet: 535-583 mg
Abbreviations: MTD = maximum tolerated dose, MAD = maximum administered dose

---

What is claimed is:

1. A method for treating breast cancer comprising administration to a patient in need of such treatment, a pharmaceutically effective amount of a pharmaceutical composition comprising a pharmaceutically effective amount of a VEGF Trap chimeric protein and a pharmaceutically effective amount of a stilbene derivative of formula (IIa)

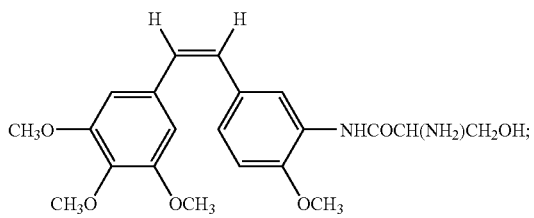

or a pharmaceutically acceptable salt of such stilbene derivative, wherein the VEGF Trap chimeric protein is SEQ ID No: 1.

2. A method for treating breast cancer, in a patient in need of such treatment, comprising administering to such patient a pharmaceutically effective amount of a combination of a VEGF Trap chimeric protein and a stilbene derivative of formula (IIa)

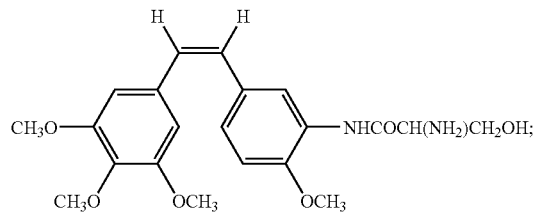

or a pharmaceutically acceptable salt of such stilbene derivative, wherein the VEGF Trap chimeric protein is SEQ ID No: 1.

3. The method according to claim 2 wherein the VEGF Trap chimeric protein and stilbene derivative are administered separately.

4. The method according to claim 2 wherein the VEGF Trap chimeric protein and stilbene derivative are administered simultaneously.

5. The method according to claim 2 wherein the stilbene derivative is in the form of a hydrochloride salt.

6. The method according to claim 2, wherein the dose of the VEGF Trap chimeric protein is about 10.0 mg/kg to about 40.0 mg/kg.

7. The method according to claim 2, wherein the dose of the stilbene derivative is about 22.3 mg/kg to about 58.0 mg/kg.

* * * * *